United States Patent
Gross et al.

(10) Patent No.: US 12,427,299 B1
(45) Date of Patent: Sep. 30, 2025

(54) PULSATILE VENTRICULAR ASSIST DEVICES

(71) Applicants: Yossi Gross, Moshav Mazor (IL); Oz Cabiri, Hod HaSharon (IL)

(72) Inventors: Yossi Gross, Moshav Mazor (IL); Oz Cabiri, Hod HaSharon (IL)

(*) Notice: Subject to any disclaimer, the term of this patent is extended or adjusted under 35 U.S.C. 154(b) by 0 days.

(21) Appl. No.: 18/795,359

(22) Filed: Aug. 6, 2024

(51) Int. Cl.
*A61M 1/00* (2006.01)
*A61M 1/12* (2006.01)
(Continued)

(52) U.S. Cl.
CPC ........ *A61M 60/178* (2021.01); *A61M 60/258* (2021.01); *A61M 60/462* (2021.01); *A61M 60/531* (2021.01); *A61M 60/835* (2021.01); *A61M 60/892* (2021.01); *A61M 60/896* (2021.01); *A61M 2205/0216* (2013.01); *A61M 2205/04* (2013.01); *A61M 2205/3303* (2013.01); *A61M 2205/3327* (2013.01); *A61M 2205/3331* (2013.01); *A61M 2205/3379* (2013.01);
(Continued)

(58) Field of Classification Search
CPC ...... A61M 2205/33; A61M 2205/3303; A61M 2205/8243; A61M 60/148; A61M 60/152; A61M 60/268; A61M 60/274; A61M 60/438; A61M 60/446; A61M 60/531; A61M 60/554; A61M 60/896
See application file for complete search history.

(56) References Cited

U.S. PATENT DOCUMENTS 3,233,607 A * 2/1966 Bolie .............. A61M 60/43
623/3.27
3,585,983 A 6/1971 Kantrowitz et al.
(Continued)

FOREIGN PATENT DOCUMENTS

WO 2005/037348 A1 4/2005
WO 2008/141325 11/2008

OTHER PUBLICATIONS

Medtronic Press Release, "New Study Demonstrates Feasibility of Novel Mechanical Sensor in Medtronic Micra Transcatheter Pacing System to Detect Atrial Contractions and Restore AV Synchrony," May 11, 2018.
(Continued)

Primary Examiner — Jon Eric C Morales
(74) Attorney, Agent, or Firm — Sughrue Mion, PLLC (57) ABSTRACT

An implantable LVAD is provided that includes a pump shaped so as to define a pump chamber. The pump includes a tubular linear motor, which includes a magnetic piston, which includes a reciprocating one-way valve configured to allow downstream blood flow and inhibit upstream blood flow; and a stator, which is configured to magnetically drive the magnetic piston with reciprocating motion, so as to pump blood downstream during downstream motion of the magnetic piston while the reciprocating one-way valve is closed. The pump further includes a spring, which is arranged to store energy during upstream motion of the magnetic piston and release the stored energy during the downstream motion of the magnetic piston. Control circuitry is configured to activate the tubular linear motor to provide pulsatile flow synchronized with cardiac cycles. Other configurations are also described.

19 Claims, 9 Drawing Sheets

(51) Int. Cl.
*A61M 60/178* (2021.01)
*A61M 60/258* (2021.01)
*A61M 60/462* (2021.01)
*A61M 60/531* (2021.01)
*A61M 60/835* (2021.01)
*A61M 60/892* (2021.01)
*A61M 60/896* (2021.01)

(52) U.S. Cl.
CPC . *A61M 2205/50* (2013.01); *A61M 2205/8212* (2013.01); *A61M 2210/125* (2013.01); *A61M 2230/005* (2013.01); *A61M 2230/04* (2013.01); *A61M 2230/40* (2013.01); *A61M 2230/63* (2013.01)

(56) References Cited

U.S. PATENT DOCUMENTS

| | | | |
|---|---|---|---|
| 3,842,440 A | 10/1974 | Karlson | |
| 3,866,604 A | 2/1975 | Curless et al. | |
| 4,102,610 A | 7/1978 | Taboada et al. | |
| 4,210,409 A | 7/1980 | Child | |
| 4,240,409 A | 12/1980 | Robinson et al. | |
| 4,245,622 A | 1/1981 | Hutchins, IV | |
| 4,375,941 A * | 3/1983 | Child | A61M 60/508 417/418 |
| 4,583,523 A | 4/1986 | Kleinke et al. | |
| 4,610,658 A | 9/1986 | Buchwald et al. | |
| 4,630,597 A | 12/1986 | Kantrowitz et al. | |
| 4,809,676 A | 3/1989 | Freeman | |
| 4,938,766 A | 7/1990 | Jarvik | |
| 5,346,476 A | 9/1994 | Elson | |
| 5,466,221 A | 11/1995 | Zadini et al. | |
| 5,514,079 A | 5/1996 | Dillon et al. | |
| 5,527,159 A | 6/1996 | Bozeman, Jr. et al. | |
| 5,554,103 A | 9/1996 | Zheng et al. | |
| 5,676,651 A * | 10/1997 | Larson, Jr. | A61M 60/237 604/33 |
| 5,693,091 A | 12/1997 | Larson, Jr. et al. | |
| 5,762,599 A | 6/1998 | Sohn | |
| 6,030,336 A | 2/2000 | Franchi | |
| 6,057,689 A | 5/2000 | Saadat | |
| 6,132,363 A | 10/2000 | Freed et al. | |
| 6,200,260 B1 | 3/2001 | Bolling | |
| 6,223,648 B1 | 5/2001 | Erickson | |
| 6,387,037 B1 | 5/2002 | Bolling et al. | |
| 6,390,969 B1 | 5/2002 | Bolling et al. | |
| 6,406,422 B1 | 6/2002 | Landesberg | |
| 6,428,464 B1 | 8/2002 | Bolling | |
| 6,450,942 B1 | 9/2002 | Lapanashvili et al. | |
| 6,468,200 B1 | 10/2002 | Fischi | |
| 6,511,413 B2 | 1/2003 | Landesberg | |
| 6,540,699 B1 | 4/2003 | Smith | |
| 6,572,652 B2 | 6/2003 | Shaknovich | |
| 6,685,621 B2 | 2/2004 | Bolling et al. | |
| 6,808,484 B1 | 10/2004 | Peters et al. | |
| 6,984,201 B2 | 1/2006 | Khaghani et al. | |
| 7,229,258 B2 | 6/2007 | Wood et al. | |
| 7,544,160 B2 | 6/2009 | Gross | |
| 7,811,221 B2 | 10/2010 | Gross | |
| 8,690,749 B1 | 4/2014 | Nunez | |
| 9,517,129 B2 | 12/2016 | Wilson et al. | |
| 10,568,999 B2 | 2/2020 | Gross | |
| 11,013,906 B2 | 5/2021 | Gross | |
| 11,395,910 B2 | 7/2022 | Gross | |
| 11,565,104 B1 | 1/2023 | Gross | |
| 2001/0027287 A1 | 10/2001 | Shmulewitz et al. | |
| 2002/0103413 A1 | 8/2002 | Bugge et al. | |
| 2002/0151761 A1 | 10/2002 | Viole et al. | |
| 2002/0173735 A1 | 11/2002 | Lewis | |
| 2003/0032853 A1 | 2/2003 | Korakianitis et al. | |
| 2003/0163020 A1 | 8/2003 | Frazier | |
| 2006/0217588 A1 * | 9/2006 | Gross | A61M 60/268 600/16 |
| 2009/0088597 A1 | 4/2009 | Frazier et al. | |
| 2010/0298929 A1 | 11/2010 | Thornton et al. | |
| 2011/0029072 A1 | 2/2011 | Gabbay | |
| 2011/0037327 A1 | 2/2011 | Denne | |
| 2016/0151553 A1 | 6/2016 | Bonde | |
| 2016/0206798 A1 | 7/2016 | Williams et al. | |
| 2017/0112985 A1 | 4/2017 | Yomtov | |
| 2018/0369469 A1 | 12/2018 | Le Duc De Lillers et al. | |

OTHER PUBLICATIONS

Voice coil actuators vs solenoids—What is the difference—Aerospace Manufacturing and Design Oct. 28, 2015.

Letsou GV, Pate TD, Gohean JR, Kurusz M, Longoria RG, Kaiser L, Smalling RW. Improved left ventricular unloading and circulatory support with synchronized pulsatile left ventricular assistance compared with continuous-flow left ventricular assistance in an acute porcine left ventricular failure model. J.Thorac Cardiovasc Surg. Nov. 2010;140(5):1181-8. doi: 10.1016/j.jtcvs.2010.03.043. Epub May 23, 2010. PMID: 20546799.

Office Action dated Mar. 19, 2025 issued in U.S. Appl. No. 19/039,635.

Office Action dated May 30, 2025 in U.S. Appl. No. 19/173,432.

* cited by examiner

PULSATILE VENTRICULAR ASSIST DEVICES

FIELD OF THE APPLICATION

The present invention relates generally to left ventricular assist devices (LVADs), and specifically to pulsatile LVADs.

BACKGROUND OF THE APPLICATION

A left ventricular assist device (LVAD) is an electromechanical device that helps pump blood from the left ventricle to partially or to completely replace the function of a failing heart. The two main types of LVADs are pulsatile LVADs and continuous-flow LVADs, also known as nonpulsatile LVADs. Pulsatile LVADs mimic the natural rhythmic action of the heart, while continuous-flow LVADs use a motor at fixed velocities, leading to constant ejection of blood to the systemic circulation.

Continuous-flow LVADs are associated with substantial side effects, including:
- altered arterial baroreceptors—reduced pulsatility leads to increased sympathetic activation and peripheral vascular resistance;
- increased cardiovascular risk factors, which include essential hypertension, stroke, chronic kidney disease, and reduced likelihood of myocardial recovery;
- increased aortic leaflet strain, which may cause aortic valve issues like fusion and regurgitation;
- gastrointestinal bleeding, which is common due to lack of pulsatility and enhanced proteolysis;
- reduced blood pressure control, which is crucial for maintaining flow and cardiac output; and
- blood pressure measurement challenges, because standard methods are less effective without pulsatile flow.

U.S. Pat. No. 11,565,104 to Gross describes a mechanical circulatory assist device that includes a stent, a coiled wire wound around the stent, and a reciprocating valve including a housing, one or more leaflets coupled to the housing, and one or more permanent magnets coupled to the housing. The magnets are arranged to interact with a magnetic field generated by the coiled wire when current flows therethrough, so as to axially move the reciprocating valve with respect to the stent when the reciprocating valve is disposed within the stent. Upstream axial motion of the reciprocating valve causes the leaflets to be in an open state in which they allow blood flow through the reciprocating valve. Downstream axial motion of the reciprocating valve causes the leaflets to be in a closed state in which they inhibit blood flow through the reciprocating valve. Other embodiments are also described.

U.S. Pat. No. 10,568,999 to Gross describes apparatus for deployment in a lumen of a blood vessel of a subject. The apparatus includes a reciprocating device configured to move downstream and upstream in the blood vessel in a reciprocating pattern to provide: (i) a first effective surface area of the device for pushing blood downstream in the blood vessel during downstream motion of the reciprocating device, and (ii) second effective surface area of the device during upstream motion of the reciprocating device. The first effective surface area is larger for pushing blood in the blood vessel than the second effective surface area. The apparatus further includes a device driver configured to drive the reciprocating device in the reciprocating pattern. Other applications are also described.

PCT Publication WO 2004/073484 to Gross et al. describes apparatus that includes an inflatable bladder, adapted to be coupled to a blood vessel of a subject carrying oxygenated blood, such that an interior of the bladder is in fluid communication with the blood. The apparatus also includes a piston in mechanical communication with the bladder; a motor, adapted to synchronize contraction and expansion of the bladder with a cardiac cycle of the subject by applying a motor force to the piston; and a spring, adapted to apply a spring force to the piston.

U.S. Pat. No. 5,693,091 to Larson, Jr. et al. describes, in one embodiment, a surgically implantable reciprocating pump that employs a check valve as the piston, which is driven by a permanent magnet linear electric motor to assist either side of the natural heart. The pump is implanted in the aorta or pulmonary artery using vascular attachment cuffs such as flexible cuffs for suturing at each end with the pump output directly in line with the artery. The pump is powered by surgically implanted rechargeable batteries. In another embodiment, pairs of pumps are provided to replace or assist the natural heart or to provide temporary blood flow throughout the body, for example, during operations to correct problems with the natural heart.

SUMMARY OF THE APPLICATION

Some embodiments of the present invention provide a left ventricular assist device (LVAD) system for treating a patient. The LVAD system comprises an implantable LVAD for implantation in the patient. The implantable LVAD comprises a pump, which is shaped so as to define a pump chamber having an upstream inflow end and a downstream outflow end. The pump comprises a tubular linear motor comprising a magnetic piston and a stator. The magnetic piston comprises a reciprocating one-way valve configured to allow downstream blood flow and inhibit upstream blood flow. The stator is configured to magnetically drive the magnetic piston with reciprocating motion, so as to pump blood downstream during downstream motion of the magnetic piston while the reciprocating one-way valve is closed. The pump further comprises a spring, which is arranged to store energy during upstream motion of the magnetic piston and release the stored energy during the downstream motion of the magnetic piston.

The LVAD further comprises outflow and inflow cannulas. The outflow cannula is couplable in fluid communication with a circulatory system of the patient at a first site, and arranged in fluid communication with the downstream outflow end of the pump chamber via a stationary one-way outflow valve of the LVAD. The stationary one-way outflow valve is configured to allow downstream blood flow from the pump chamber to the outflow cannula and to inhibit upstream blood flow from the outflow cannula to the pump chamber. The inflow cannula is couplable in fluid communication with the circulatory system at a second site upstream of the first site, and arranged in fluid communication with the upstream inflow end of the pump chamber.

The LVAD system further comprises a cardiac sensor and control circuitry. The cardiac sensor is configured to sense one or more features of a plurality of cardiac cycles of the heart. The control circuitry is coupled to the cardiac sensor and configured to activate the tubular linear motor to provide pulsatile flow synchronized with the cardiac cycles by, during each of the cardiac cycles:
activating the stator of the tubular linear motor, during at least a portion of systole, to move the magnetic piston downstream during a first period of time, and activating the stator of the tubular linear motor, during at least a portion of diastole, to move the magnetic piston upstream during a second period of time.

The motion of the magnetic piston upstream during the second period stores energy in the spring, which releases the stored energy during systole, thereby reducing the amount of energy that the tubular linear motor must apply during systole in order to achieve a given amount of downstream motion of the magnetic piston. This allocation of activation of the tubular linear motor between diastole and systole reduces the peak power consumed by the tubular linear motor during systole, which may reduce the motor's demands on a power source (e.g., comprising one or more batteries) of the LVAD system. For example, the control circuitry and the spring may be configured such that, during each of the cardiac cycles, peak power consumed by the tubular linear motor during systole is no more than three times, such as no more than two times, peak power consumed by the tubular linear motor during diastole.

The activation of the tubular linear motor to pump blood downstream only during a portion of systole provides pulsatile blood flow, which mimics the healthy heart's natural function. Pulsatility in blood flow is considered crucial for normal organ function, particularly for critical organs such as the kidney, liver, brain, and heart.

In an application of the present invention, the control circuitry is configured to activate the tubular linear motor to provide pulsatile flow synchronized with the cardiac cycles by:

during at least a portion of systole of each of the cardiac cycles, activating the stator of the tubular linear motor to move the magnetic piston downstream at a velocity set based on a target stroke volume and a target stroke duration, and during at least a portion of diastole of each of the cardiac cycles, activating the stator of the tubular linear motor to move the magnetic piston upstream.

Thus, the control circuitry uses the target stroke volume and target stroke duration as inputs to calculate the velocity of the magnetic piston, such that the magnetic piston moves during the entirety of the target stroke duration, rather than moving the magnetic piston at a predetermined rate for the amount of time necessary to provide the target stroke volume. Utilizing the entire available target stroke duration may reduce peak energy consumption and/or provide pumping that more closely mimics the natural physiological pumping.

There is therefore provided, in accordance with an application of the present invention, a left ventricular assist device (LVAD) system for treating a patient, the LVAD system including:

(i) an implantable LVAD for implantation in the patient, the LVAD including:
  a stationary one-way outflow valve;
  a pump, which (a) is shaped so as to define a pump chamber having an upstream inflow end and a downstream outflow end, and (b) includes:
    a tubular linear motor, which includes (1) a magnetic piston, which includes a reciprocating one-way valve configured to allow downstream blood flow and inhibit upstream blood flow; and (2) a stator, which is configured to magnetically drive the magnetic piston with reciprocating motion, so as to pump blood downstream during downstream motion of the magnetic piston while the reciprocating one-way valve is closed;
    a spring, which is arranged to store energy during upstream motion of the magnetic piston and release the stored energy during the downstream motion of the magnetic piston;
  an outflow cannula, which is (1) couplable in fluid communication with a circulatory system of the patient at a first site, and (2) arranged in fluid communication with the downstream outflow end of the pump chamber via the stationary one-way outflow valve, wherein the stationary one-way outflow valve is configured to allow downstream blood flow from the pump chamber to the outflow cannula and to inhibit upstream blood flow from the outflow cannula to the pump chamber; and
  an inflow cannula, which is (1) couplable in fluid communication with the circulatory system at a second site upstream of the first site, and (2) arranged in fluid communication with the upstream inflow end of the pump chamber;

(ii) a cardiac sensor, configured to sense one or more features of a plurality of cardiac cycles of a heart of the patient; and (iii) control circuitry, which is coupled to the cardiac sensor and configured to activate the tubular linear motor to provide pulsatile flow synchronized with the cardiac cycles by, during each of the cardiac cycles:
  activating the stator of the tubular linear motor, during a first portion of the cardiac cycle, to move the magnetic piston downstream during a first period of time, and
  activating the stator of the tubular linear motor, during a second portion of the cardiac cycle, to move the magnetic piston upstream during a second period of time,
  wherein the first portion of the cardiac cycle is at least a portion of one of systole or diastole, and the second portion of the cardiac cycle is at least a portion of the other of systole or diastole.

For some applications, the first period of time has a first duration, and the second period of time has a second duration greater than the first duration.

For some applications, the spring includes an elastic spring.

For some applications, the spring includes a magnetic spring.

For some applications:
the implantable LVAD further includes a stationary one-way inflow valve,
the inflow cannula is arranged in fluid communication with the upstream inflow end of the pump chamber via the stationary one-way inflow valve, and
the stationary one-way inflow valve is configured to allow downstream blood flow from the inflow cannula to the pump chamber and to inhibit upstream blood flow from the pump chamber to the inflow cannula.

For some applications, the LVAD system further includes a battery arranged to provide power to the tubular linear motor.

For any of the applications described above, the control circuitry and the spring may be configured such that, during each of the cardiac cycles, peak power consumed by the tubular linear motor during the first portion of the cardiac cycle is no more than three times peak power consumed by the tubular linear motor during the second portion of the cardiac cycle. For some of these applications, the control circuitry and the spring are configured such that, during each of the cardiac cycles, the peak power consumed by the tubular linear motor during the first portion of the cardiac cycle is no more than two times the peak power consumed by the tubular linear motor during the second portion of the cardiac cycle.

There is further provided, in accordance with an application of the present invention, a left ventricular assist device (LVAD) system for treating a patient, the LVAD system including:
  (i) an implantable LVAD for implantation in the patient, the LVAD including:
    a stationary one-way outflow valve; and
    a pump, which (a) is shaped so as to define a pump chamber having an upstream inflow end and a downstream outflow end, and (b) which includes:
      a tubular linear motor, which includes (1) a magnetic piston, which includes a reciprocating one-way valve configured to allow downstream blood flow and inhibit upstream blood flow; and (2) a stator, which is configured to magnetically drive the magnetic piston with reciprocating motion, so as to pump blood downstream during downstream motion of the magnetic piston while the one-way reciprocating valve is closed;
      an outflow cannula, which is (1) couplable in fluid communication with a circulatory system of the patient at a first site, and (2) arranged in fluid communication with the downstream outflow end of the pump chamber via the stationary one-way outflow valve, wherein the stationary one-way outflow valve is configured to allow downstream blood flow from the pump chamber to the outflow cannula and to inhibit upstream blood flow from the outflow cannula to the pump chamber; and
      an inflow cannula, which is (1) couplable in fluid communication with the circulatory system at a second site upstream of the first site, and (2) arranged in fluid communication with the upstream inflow end of the pump chamber;
  (ii) a cardiac sensor, configured to sense one or more features of a plurality of cardiac cycles of a heart of the patient; and
  (iii) control circuitry, which is coupled to the cardiac sensor and configured to activate the tubular linear motor to provide pulsatile flow synchronized with the cardiac cycles by:
    during a first portion of each of the cardiac cycles, activating the stator of the tubular linear motor to move the magnetic piston downstream at a velocity set based on a target stroke volume and a target stroke duration, and
    during a second portion of each of the cardiac cycles, activating the stator of the tubular linear motor to move the magnetic piston upstream,
    wherein the first portion of each of the cardiac cycles is at least a portion of one of systole or diastole, and the second portion of each of the cardiac cycles is at least a portion of the other of systole or diastole.

For some applications, the LVAD system further includes a left atrial pressure sensor, which is configured to sense left atrial pressure, and the control circuitry is configured to set the target stroke volume at a level that prevents the sensed left atrial pressure from exceeding a threshold pressure.

For some applications:
  the implantable LVAD further includes a stationary one-way inflow valve,
  the inflow cannula is arranged in fluid communication with the upstream inflow end of the pump chamber via the stationary one-way inflow valve, and
  the stationary one-way inflow valve is configured to allow downstream blood flow from the inflow cannula to the pump chamber and to inhibit upstream blood flow from the pump chamber to the inflow cannula.

For some applications, the LVAD system further includes a battery arranged to provide power to the tubular linear motor.

For any of the applications described above, the LVAD system may further include one or more activity sensors, which are configured to sense a level of activity of the patient, and the control circuitry may be configured to set the target stroke volume responsively to the sensed level of activity of the patient. For some applications, the one or more activity sensors include an accelerometer, which is configured to sense the level of activity of the patient. For some applications, the one or more activity sensors include a respiration sensor, which is configured to sense the level of activity of the patient by sensing one or more parameters of respiration of the patient. For some applications, the respiration sensor is configured to detect transthoracic impedance.

For any of the applications described above, the control circuitry may be configured to set the target stroke duration responsively to the sensed one or more features of the plurality of cardiac cycles. For some applications, the control circuitry is configured to set the target stroke duration responsively to a duration of systole of the plurality of cardiac cycles. For some applications, the control circuitry is configured to set the target stroke duration equal to a fraction of the duration of systole of the plurality of cardiac cycles. For some applications, the control circuitry is configured to set the target stroke duration responsively to a duration of diastole of the plurality of cardiac cycles. For some applications, the control circuitry is configured to set the target stroke duration equal to a fraction of the duration of diastole of the plurality of cardiac cycles.

There is still further provided, in accordance with an application of the present invention, a left ventricular assist device (LVAD) system for treating a patient, the LVAD system including:
  (i) an implantable LVAD for implantation in the patient, the LVAD including:
    a stationary one-way outflow valve;
    a pump, which (a) is shaped so as to define a pump chamber having an upstream inflow end and a downstream outflow end, and (b) includes:
      a tubular linear motor, which includes (1) a magnetic piston, which includes a reciprocating one-way valve configured to allow downstream blood flow and inhibit upstream blood flow; and (2) a stator, which is configured to magnetically drive the magnetic piston with reciprocating motion, so as to pump blood downstream during downstream motion of the magnetic piston while the reciprocating one-way valve is closed, wherein an inner surface of the pump chamber and an outer surface of the magnetic piston have respective rectangular cross-sections perpendicular to a central longitudinal axis of the pump chamber;
      an outflow cannula, which is (1) couplable in fluid communication with a circulatory system of the patient at a first site, and (2) arranged in fluid communication with the downstream outflow end of the pump chamber via the stationary one-way outflow valve, wherein the stationary one-way outflow valve is configured to allow downstream blood flow from the pump chamber to the outflow cannula and to inhibit upstream blood flow from the outflow cannula to the pump chamber; and an inflow cannula, which is (1) couplable in fluid communication with the circulatory system at a second site upstream of the first site, and (2) arranged in fluid communication with the upstream inflow end of the pump chamber;

(ii) a cardiac sensor, configured to sense one or more features of a plurality of cardiac cycles of a heart of the patient; and (iii) control circuitry, which is coupled to the cardiac sensor and configured to activate the tubular linear motor to provide pulsatile flow synchronized with the cardiac cycles.

For some applications, the control circuitry is configured to activate the tubular linear motor to provide the pulsatile flow synchronized with the cardiac cycles by:

during a first portion of each of the cardiac cycles, activating the stator of the tubular linear motor to move the magnetic piston downstream, during a second portion of each of the cardiac cycles, activating the stator of the tubular linear motor to move the magnetic piston upstream, wherein the first portion of each of the cardiac cycles is at least a portion of one of systole or diastole, and the second portion of each of the cardiac cycles is at least a portion of the other of systole or diastole.

There is additionally provided, in accordance with an application of the present invention, a method including:

accessing a thoracic cavity of a patient; and transthoracically implanting a left ventricular assist device (LVAD) in the patient by:

transmurally inserting an inflow cannula of the LVAD into a left atrial appendage (LAA) of a heart, and securing the inflow cannula to a left atrial wall, and anastomosing an outflow cannula of the LVAD to a descending aorta.

For some applications, accessing the thoracic cavity includes performing a left thoracotomy.

For some applications:

inserting the inflow cannula into the LAA includes passing an inflow end opening of the inflow cannula through a mitral valve into a left ventricle, and securing the inflow cannula to the left atrial wall holds the inflow end opening of the inflow cannula in the left ventricle.

For some applications, implanting the LVAD includes identifying that the patient suffers from mitral regurgitation, and passing the inflow end opening of the inflow cannula through the mitral valve into the left ventricle causes leaflets of the mitral valve to at least partially contact an outer surface of the inflow cannula during systole, thereby reducing mitral regurgitation.

For some applications:

inserting the inflow cannula into the LAA includes positioning an inflow end opening of the inflow cannula in a left atrium, and securing the inflow cannula to the left atrial wall holds the inflow end opening of the inflow cannula in the left atrium.

The present invention will be more fully understood from the following detailed description of embodiments thereof, taken together with the drawings, in which:

DETAILED DESCRIPTION OF APPLICATIONS

Figure 1:
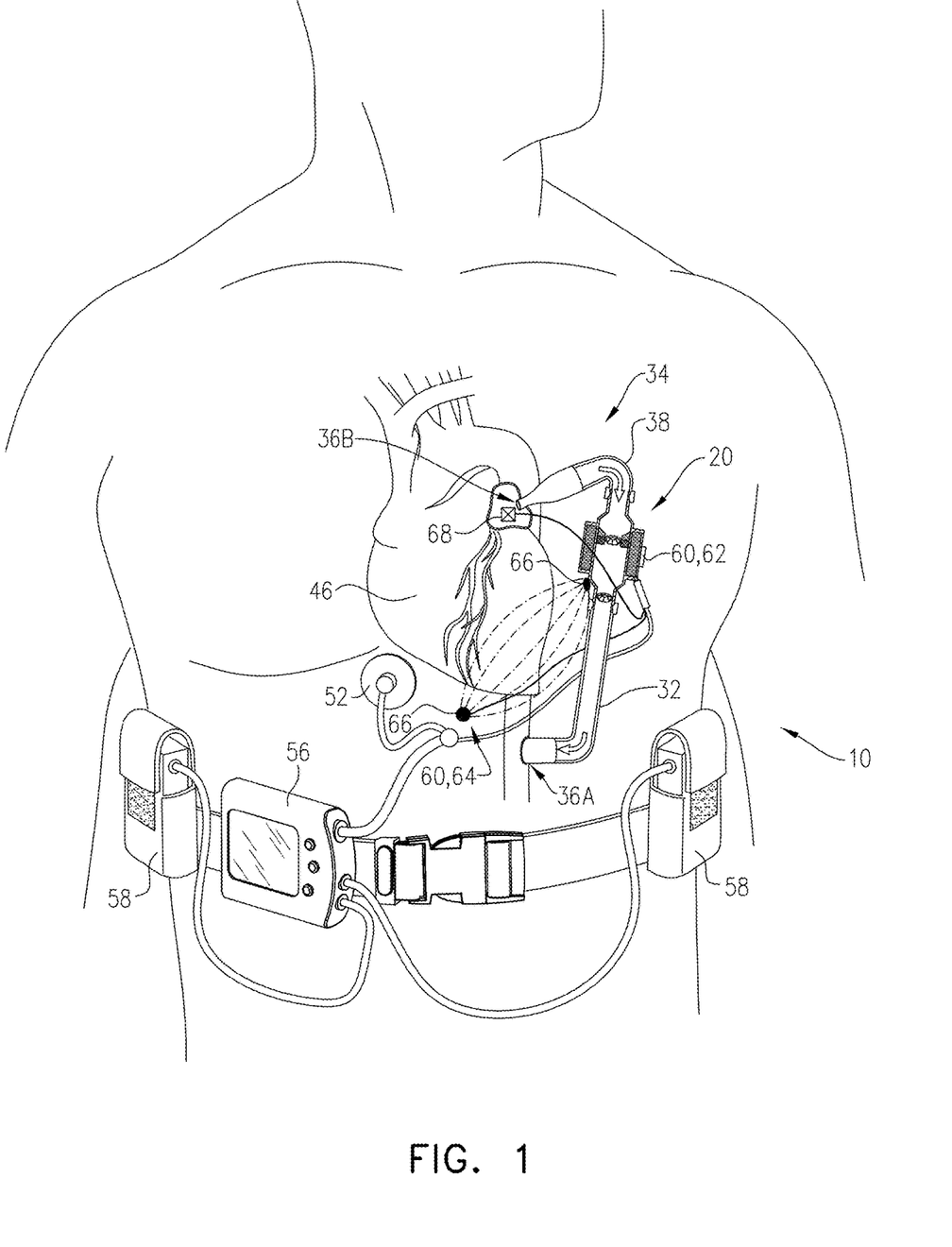
FIG. 1 is a schematic cross-sectional illustration of a left ventricular assist device (LVAD) system applied to a patient, in accordance with an application of the present invention.

FIG. 1 is a schematic cross-sectional illustration of a left ventricular assist device (LVAD) system 10 applied to a patient, in accordance with an application of the present invention.

Figure 2:
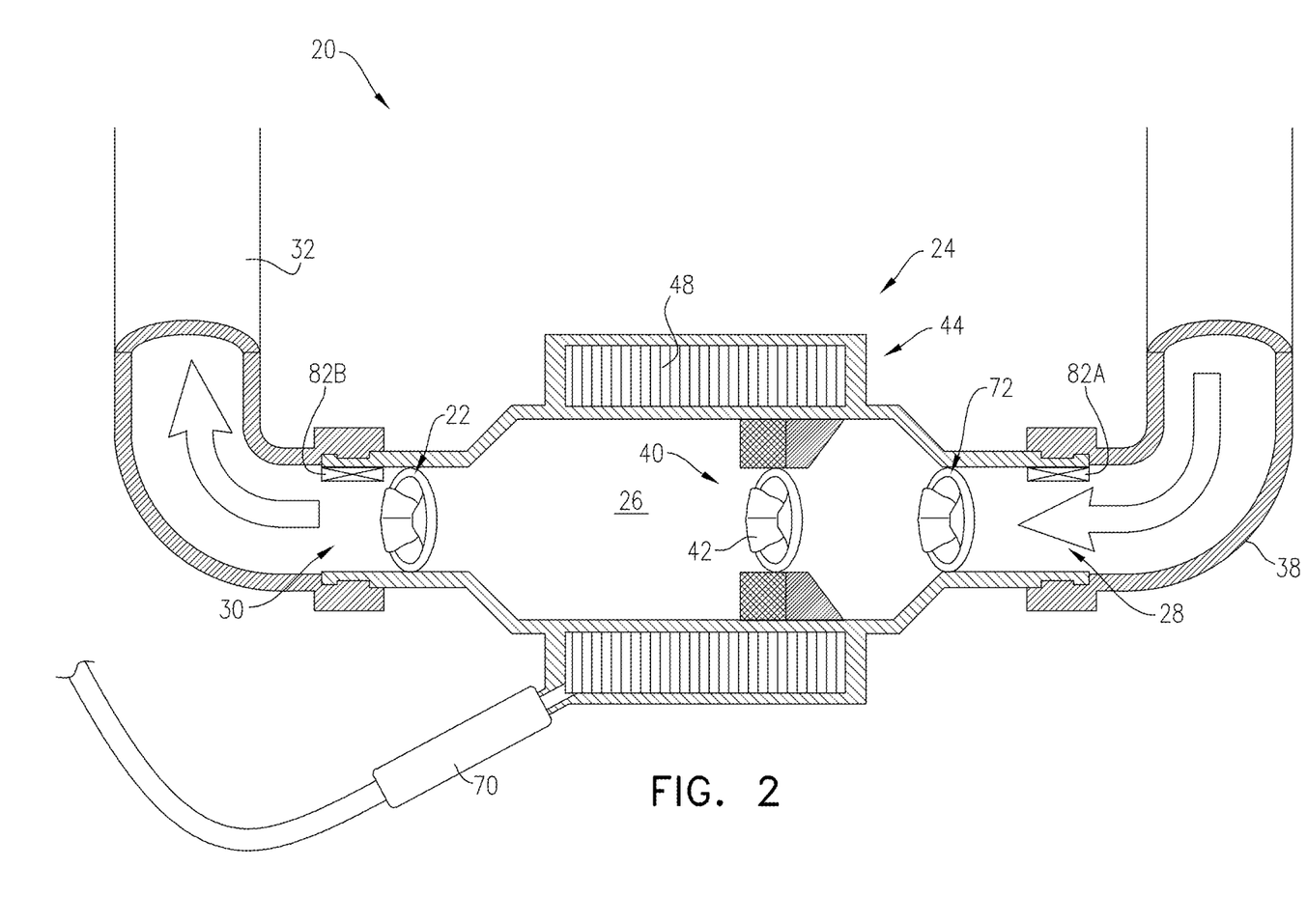
FIG. 2 is a schematic illustration of an implantable LVAD of the LVAD system of FIG. 1, in accordance with an application of the present invention.

FIG. 2 is a schematic illustration of an implantable LVAD 20 of LVAD system 10, in accordance with an application of the present invention.

LVAD 20 comprises:

a stationary one-way outflow valve 22;

a pump 24, which (a) is shaped so as to define a pump chamber 26 having an upstream inflow end 28 and a downstream outflow end 30;

an outflow cannula 32, which is (a) couplable in fluid communication with a circulatory system 34 of the patient at a first site 36A, and (b) arranged in fluid communication with downstream outflow end 30 of pump chamber 26 via stationary one-way outflow valve 22; stationary one-way outflow valve 22 is configured to allow downstream blood flow from pump chamber 26 to outflow cannula 32 and to inhibit upstream blood flow from outflow cannula 32 to pump chamber 26; and an inflow cannula 38, which is (a) couplable in fluid communication with circulatory system 34 at a second site 36B upstream of first site 36A, and (b) arranged in fluid communication with upstream inflow end 28 of pump chamber 26.

Pump 24 typically comprises a tubular linear motor 44, which comprises:

a magnetic piston 40, which comprises a reciprocating one-way valve 42 configured to allow downstream blood flow and inhibit upstream blood flow; and a stator 48, which is configured to magnetically drive magnetic piston 40 with reciprocating motion (such that magnetic piston 40 serves as the slider of tubular linear motor 44), so as to pump blood downstream during downstream motion of magnetic piston 40 while reciprocating one-way valve 42 is closed.

Stator 48 comprises coil windings, as is known in the tubular linear motor art. Tubular linear motor 44 is typically configured a levitating linear motor, in the sense that magnetic piston 40 slides within stator 48 without bearings, i.e., tubular linear motor 44 is bearingless.

LVAD 20 typically generates laminar blood flow without turbulence, which results in low shear stress on red blood cells, thereby reducing the likelihood of hemolysis and thrombosis.

LVAD system 10 typically further comprises:
- a cardiac sensor 52, configured to sense one or more features of a plurality of cardiac cycles of a heart 46;
- control circuitry 56, which is coupled to cardiac sensor 52 and configured to activate tubular linear motor 44 to provide pulsatile flow synchronized with the cardiac cycles; and
- typically, a power source 58 (e.g., comprising one or more batteries) arranged to provide power to tubular linear motor 44.

Typically, cardiac sensor 52 comprises one or more implantable or external ECG electrodes, which are configured to sense components of an ECG of the patient. Other components of cardiac sensor 52, such as electronics, may be located either within LVAD 20 or in an external component of LVAD system 10, such as circuitry 56.

For some applications, at least a portion of control circuitry 56 and/or power source 58 are configured to be placed outside the patient's body. For these applications, LVAD system 10 may further comprise a percutaneous lead 70, which couples control circuitry 56 to LVAD 20 and/or power source 58. For example, percutaneous lead 70 may have a small diameter, e.g., 2 mm, which may reduce the risk of infection. Alternatively, control circuitry 56 and/or power source 58 may be wirelessly coupled to LVAD 20.

For some applications, at least a portion of an internal surface of pump chamber 26 is coated with a diamond-like carbon (DLC) coating.

Typically, the blood-contacting surfaces of LVAD 20 comprise bioprosthetic materials.

In an application of the present invention, LVAD system 10 comprises one or more activity sensors 60, which are configured to sense a level of activity of the patient.

For example, the one or more activity sensors 60 may comprise one or more of the following sensors:
- an accelerometer 62, which is configured to sense the level of activity of the patient by sensing motion of the patient, and/or
- a respiration sensor 64, which is configured to sense the level of activity of the patient by sensing one or more parameters of respiration of the patient; for example, respiration sensor 64 may measure changes in respiration rate and/or lung volume based on transthoracic impedance, and, to this end, may comprise at least two electrodes 66 (which are typically implantable) between which impedance of one or both lungs is measured.

In an application of the present invention, control circuitry 56 is configured to adapt the stroke volume provided by tubular linear motor 44 according the metabolic demands, as indicated by the level of activity of the patient sensed using the one or more activity sensors 60. This may mimic to some extent the healthy heart, in which the stroke volume varies according to metabolic demands (in accordance with the Frank-Starling law).

In an application of the present invention, control circuitry 56 is configured to activate tubular linear motor 44 to provide pulsatile flow synchronized with the cardiac cycles by:
- during at least a portion of systole of each of the cardiac cycles, activating stator 48 to move magnetic piston 40 downstream at a velocity set based on a target stroke volume and a target stroke duration, and
- during at least a portion of diastole of each of the cardiac cycles, activating stator 48 to move magnetic piston 40 upstream.

Thus, control circuitry 56 uses the target stroke volume and target stroke duration as inputs to calculate (e.g., mathematically or using a lookup table) the velocity of magnetic piston 40, such that magnetic piston 40 moves during the entirety of the target stroke duration, rather than moving the magnetic piston at a predetermined rate for the amount of time necessary to provide the target stroke volume. Utilizing the entire available target stroke duration may reduce peak energy consumption and/or provide pumping that more closely mimics the natural physiological pumping.

Typically, LVAD 20 is configurable to provide a stroke volume of 1-90 cc per cardiac cycle. LVAD 20 controls the provided stroke volume by setting a distance that magnetic piston 40 moves during pumping during each cardiac cycle. Typically, LVAD 20 is configured to set the stroke volume to less than a healthy heart's natural stroke volume (e.g., less than 80%-90% of a healthy heart's natural stroke volume).

For some applications, control circuitry 56 is configured to allow the target stroke volume to be manually programmed by a physician.

For some applications, control circuitry 56 is configured to set the target stroke volume responsively to the level of activity of the patient sensed using one or more activity sensors 60.

For some applications, control circuitry 56 is configured to set the target stroke duration responsively to the sensed one or more features of the plurality of cardiac cycles, such as responsively to a duration of systole of the plurality of cardiac cycles, e.g., equal to a fraction of the duration of systole of the plurality of cardiac cycles.

For some applications, LVAD system 10 further comprises a left atrial pressure sensor 68, which is configured to sense left atrial pressure. Control circuitry 56 is configured to set the target stroke volume at a level that prevents the sensed left atrial pressure from exceeding a threshold pressure. For example, the threshold pressure may be 12-15 mm Hg.

Reference is again made to FIG. 2. For some applications, LVAD system 10 further comprises an upstream pressure sensor 82A and/or a downstream pressure sensor 82B, which are configured to measure blood pressure of blood entering upstream inflow end 28 of pump chamber 26 and blood exiting downstream outflow end 30 of pump chamber 26, respectively. For some applications, LVAD system 10 is configured to:
- detect a malfunction and/or blockage of pump 24 based on a difference between the pressures sensed by upstream and downstream pressure sensors 82A and 82B, in which case LVAD system 10 typically ceases pumping and generates an alert to the patient and/or a healthcare provider,
- reduce the stroke volume if the pressure sensed by downstream pressure sensor 82B exceeds a threshold value (e.g., 120 mm Hg), which may be harmful for the patient, and/or
- reduce the stroke volume if the pressure sensed by upstream pressure sensor 82A falls below a threshold value, because insufficient inflow blood is available to provide the desired stroke volume.

Alternatively or additionally, LVAD system 10 may further comprise a flow sensor, which is configured to measure a velocity and/or volume of blood flow through pump 24.

For some applications, LVAD system 10 is configured to reduce the stroke volume if the current consumed by the tubular linear motor 44 exceeds a threshold value (typically measured in mA); the threshold value typically varies based on the stroke volume (e.g., based on a graph). The stroke volume is typically reduced until the current consumption falls below the threshold value for the reduced stroke volume. This feature may prevent tubular linear motor 44 from consuming more current than can or should be provided by the one or more batteries of the system.

Reference is made to FIG. 2. For some applications, implantable LVAD 20 further comprises a stationary one-way inflow valve 72. Inflow cannula 38 is arranged in fluid communication with upstream inflow end 28 of pump chamber 26 via stationary one-way inflow valve 72. Stationary one-way inflow valve 72 is configured to allow downstream blood flow from inflow cannula 38 to pump chamber 26 and to inhibit upstream blood flow from pump chamber 26 to inflow cannula 38. Stationary one-way inflow valve 72 may prevent upstream propagation of any shock waves that may be generated by upstream motion of magnetic piston 40.

Alternatively, as shown in the other figures, implantable LVAD 20 does not comprise stationary one-way inflow valve 72.

Figure 3A:
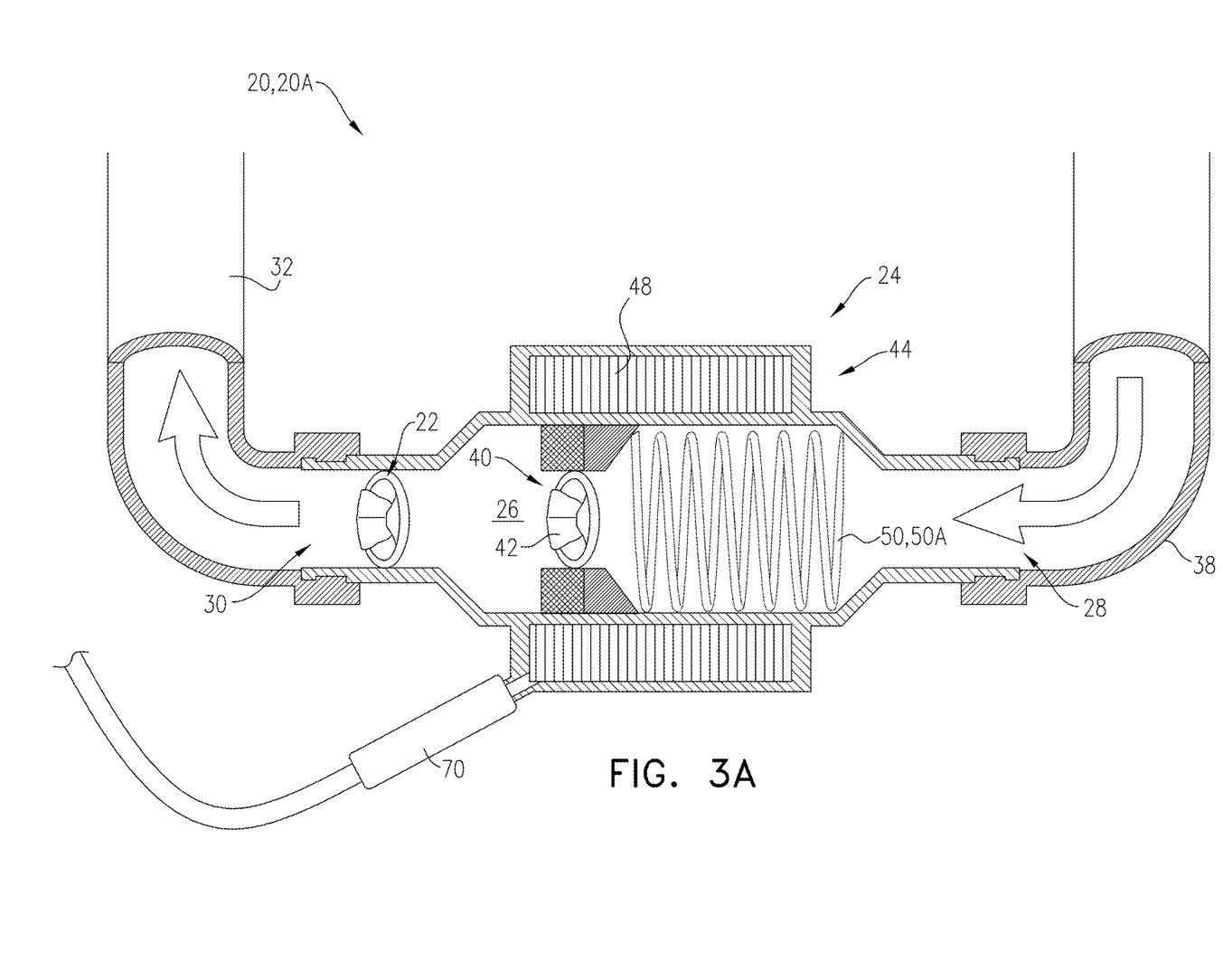
FIGS. 3A-B are schematic cross-sectional illustrations of alternative configurations of the implantable LVAD of FIG. 2, in accordance with respective applications of the present invention.
Figure 3B:
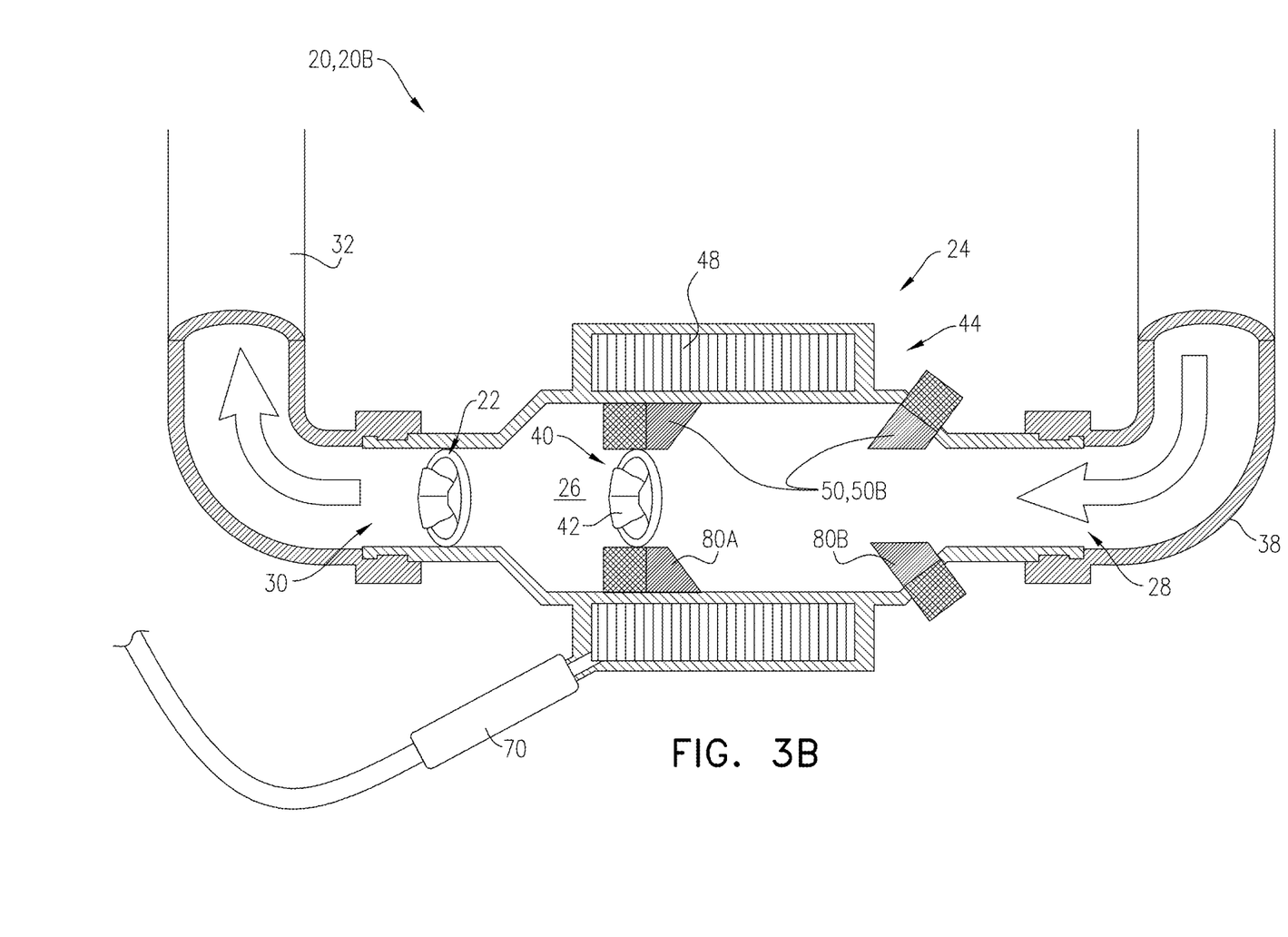

Reference is now made to FIGS. 3A-B, which are schematic cross-sectional illustrations of alternative configurations of implantable LVAD 20, in accordance with respective applications of the present invention.

In these configurations of LVAD 20, pump 24 further comprises a spring 50, which is arranged to store energy during upstream motion of magnetic piston 40 and release the stored energy during the downstream motion of magnetic piston 40. Control circuitry 56 is configured to activate tubular linear motor 44 to provide pulsatile flow synchronized with the cardiac cycles by, during each of the cardiac cycles:

activating stator 48, during at least a portion of systole, to move magnetic piston 40 downstream during a first period of time having a first duration, and activating stator 48, during at least a portion of diastole, to move magnetic piston 40 upstream during a second period of time having a second duration.

The motion of magnetic piston 40 upstream during the second period stores energy in spring 50. Spring 50 releases the stored energy during systole, thereby reducing the amount of energy that tubular linear motor 44 must apply during systole in order to achieve a given amount of downstream motion of magnetic piston 40. This allocation of activation of tubular linear motor 44 between diastole and systole reduces the peak power consumed by tubular linear motor 44 during systole, which may reduce the motor's demands on power source 58 (which, as mentioned above, may comprise one or more batteries). For example, control circuitry 56 and spring 50 may be configured such that, during each of the cardiac cycles, peak power consumed by tubular linear motor 44 during systole is no more than three times, such as no more than two times, peak power consumed by tubular linear motor 44 during diastole.

For some applications, the second duration is greater than the first duration.

For some applications, such as shown in FIG. 3A, LVAD 20 comprises an implantable LVAD 20A, and spring 50 comprises an elastic spring 50A. For example, spring 50A may comprise a compression spring (as shown) or an extension spring (configuration not shown), or any other type of spring known in the mechanical arts. Spring 50A is coupled between magnetic piston 40 and a location fixed with respect to pump chamber 26.

For other applications, such as shown in FIG. 3B, LVAD 20 comprises an implantable LVAD 20B, and spring 50 comprises a magnetic spring 50B, which comprises a first moveable magnet 80A and a second stationary magnet 80B. Magnetic piston 40 comprises first moveable magnet 80A. First moveable magnet 80A may be one of the magnets of magnetic piston 40 used for the motorized motion of the magnetic piston, such as shown, or may be a separate magnet coupled to magnetic piston 40. Second stationary magnet 80B is coupled to pump 24 at a fixed location with respect to pump chamber 26, such as at a location axially upstream of magnetic piston 40, e.g., axially between magnetic piston 40 and upstream inflow end 28 of pump chamber 26. For example, the respective magnetic poles of first and second magnets 80A and 80B may be oriented in opposite directions, such that poles having the same polarity face each other.

Figure 4:
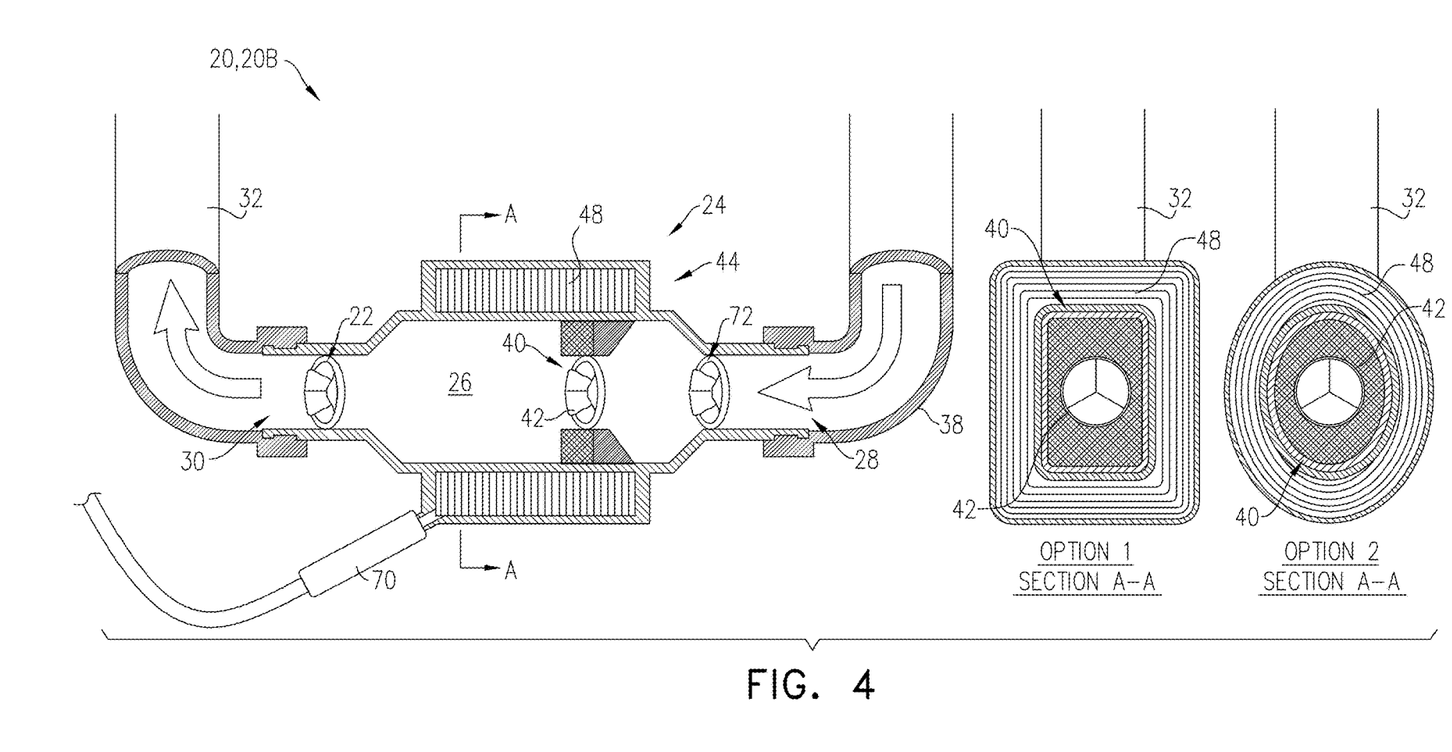
FIG. 4 is a schematic illustration of yet additional configurations of the implantable LVAD of FIG. 2, in accordance with respective applications of the present invention.

Reference is now made to FIG. 4, which is a schematic illustration of yet additional configurations of implantable LVAD 20, in accordance with respective applications of the present invention. The features of these configurations may be implemented in combination with the features of any of the other configurations of implantable LVAD 20 described herein, mutatis mutandis, and like reference numerals refer to like parts.

In these configurations, an inner surface of pump chamber 26 and an outer surface of magnetic piston 40 of pump 24 have respective elongate non-circular cross-sections perpendicular to a central longitudinal axis of pump chamber 26, each of which cross-sections has a greatest dimension in one direction that is greater than a greatest dimension in a perpendicular direction. For example, the elongate non-circular cross-sections may be rectangular or elliptical, as shown. The elongate cross-sections provide a lower profile than a circular configuration, which may facilitate subcutaneous implantation. For example, rectangular cross-sections may provide a more accurate mechanism than an elliptical cross-sectional shape, because the outer surface of magnetic piston 40 may experience less friction with the inner surface of pump chamber 26 and be less likely to jam.

Figure 5A:
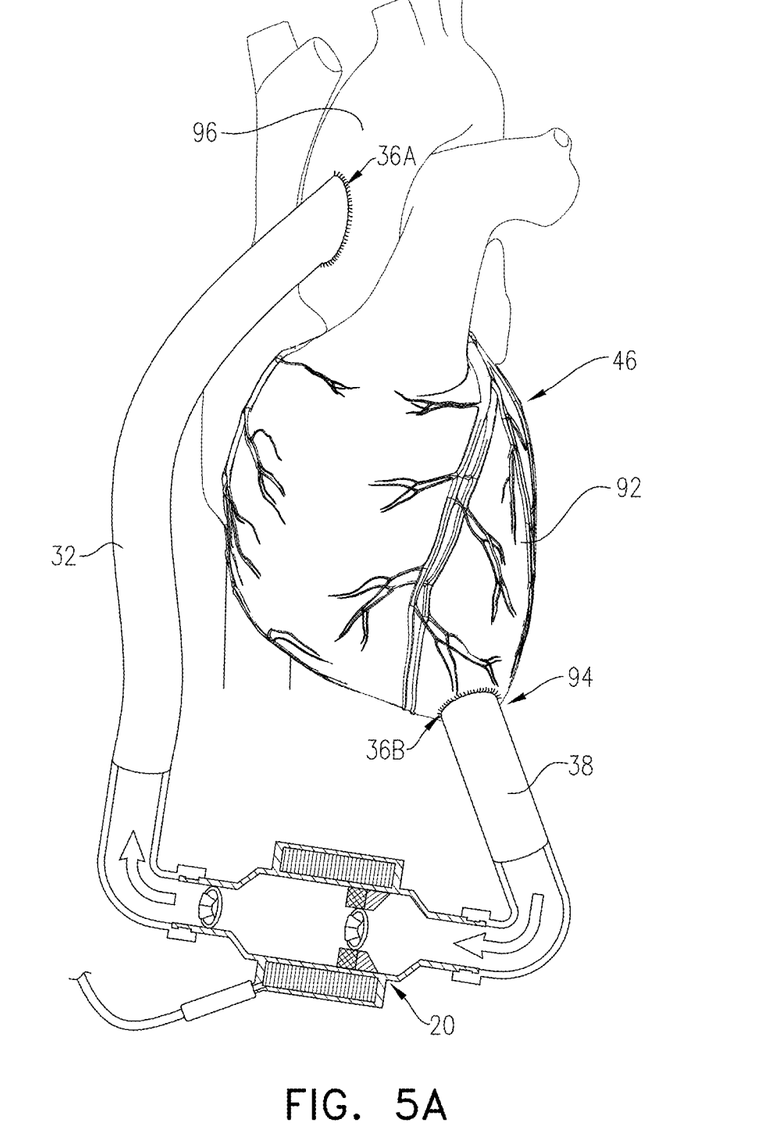
FIGS. 5A-D are schematic illustrations of methods of coupling an implantable LVAD in fluid communication with a circulatory system of a patient.
Figure 5B:
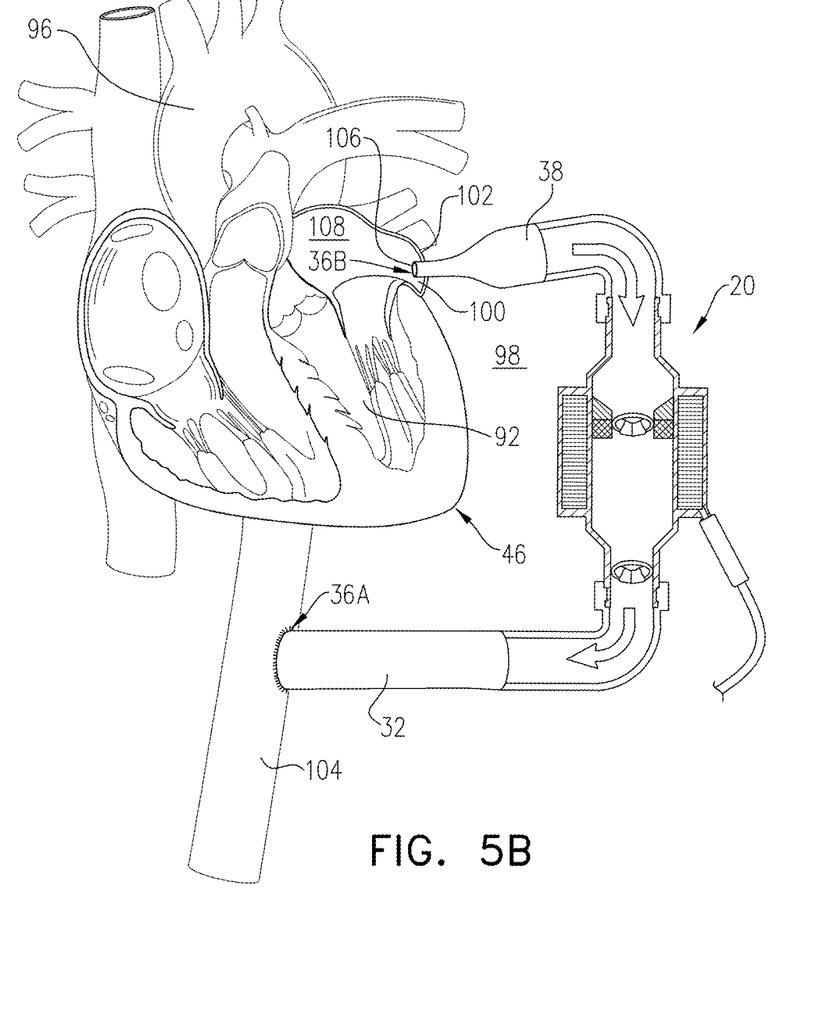
Figure 5C:
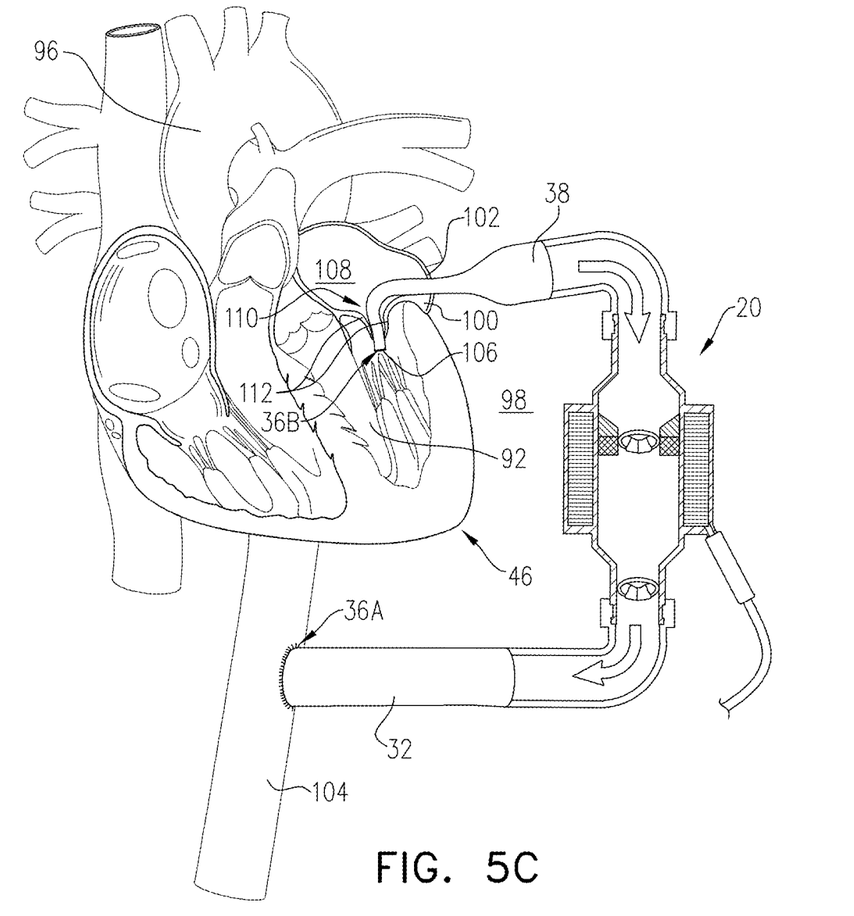

Reference is now made to FIGS. 5A-C, which are schematic illustrations of methods of coupling an implantable LVAD in fluid communication with circulatory system 34.

FIG. 5A shows a conventional coupling technique, in which inflow cannula 38 is inserted into a left ventricle 92 at the left ventricle's apex 94, and outflow cannula 32 is coupled to an ascending aorta 96. In this conventional technique, a thoracic cavity 98 of the patient is accessed, typically by performing a sternotomy, which is commonly used for implanting LVADs, in order to provide access to both the left ventricle's apex 94 and ascending aorta 96.

FIGS. 5B and 5C show additional coupling techniques, in accordance with respective applications of the present invention. In these techniques, thoracic cavity 98 of the patient is accessed, typically by performing a left thoracotomy. As is known in the general surgical arts, a left thoracotomy is generally less traumatic than the sternotomy commonly used in conventional LVAD implantation techniques.

After accessing thoracic cavity 98, an LVAD (either LVAD 20 or an LVAD known in the art) is transthoracically implanted in the patient by:

transmurally inserting an inflow cannula of the LVAD into a left atrial appendage (LAA) 100 of heart 46, and securing the inflow cannula to a left atrial wall 102 (such as by stitching around the inflow cannula on an external surface of left atrial wall 102), and anastomosing an outflow cannula of the LVAD to a descending aorta 104.

Generally, it is easier to attach the outflow cannula to descending aorta 104 than ascending aorta 96, because of the easier access available to the descending aorta than to the ascending aorta.

In the technique shown in FIG. 5B, an inflow end opening 106 of the inflow cannula is positioned in a left atrium 108 (either in LAA 100 or outside LAA 100). Securing the inflow cannula to left atrial wall 102 holds inflow end opening 106 of the inflow cannula in left atrium 108.

In the technique shown in FIG. 5C, inserting the inflow cannula into LAA 100 comprises passing inflow end opening 106 of the inflow cannula through a mitral valve 110 into left ventricle 92. Securing the inflow cannula to left atrial wall 102 holds inflow end opening 106 of the inflow cannula in left ventricle 92.

For some applications, in the technique shown in FIG. 5C, implanting the LVAD comprises identifying that the patient suffers from mitral regurgitation, and passing inflow end opening 106 of the inflow cannula through mitral valve 110 into left ventricle 92 causes leaflets 112 of the mitral valve to at least partially contact an outer surface of the inflow cannula during systole, thereby reducing mitral regurgitation.

Figure 5D:
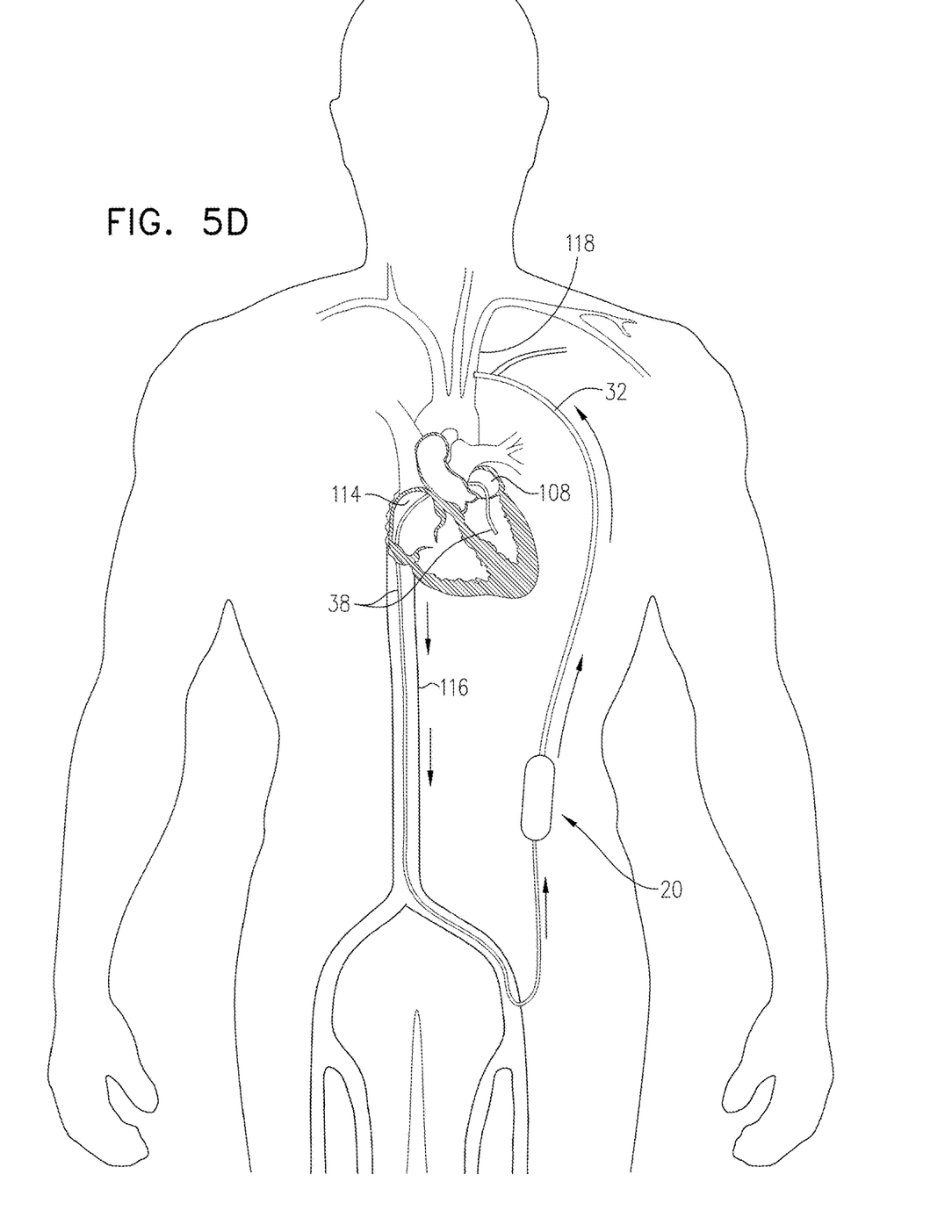

FIG. 5D shows another coupling technique, in which the inflow cannula is inserted into left ventricle 92, such as via mitral valve 110, for example by one of the following approaches:
 transeptally via a right atrium 114 and an inferior vena cava 116 (e.g., using a transfemoral venous approach), such as shown,
 via LAA 100, such as described hereinabove with reference to FIG. 5C, or
 through the left ventricle's apex 94, such as described hereinabove with reference to FIG. 5A.

Alternatively, the inflow cannula is inserted into left atrium 108 via LAA 100, such as described hereinabove with reference to FIG. 5B.

For some applications, such as shown in FIG. 5D, the outflow cannula is coupled to a left subclavian artery 118, typically by anastomosis. Alternatively, for some applications, the outflow cannula is coupled to descending aorta 104, typically by anastomosis, such as described hereinabove with reference to FIG. 5C.

Alternatively, for some applications (configurations not shown), the outflow cannula is coupled to ascending aorta 96, typically by anastomosis, and/or the inflow cannula is inserted into left ventricle 92 through a wall of ascending aorta 96 and an aortic valve.

Reference is made to FIGS. 1-5D. In some applications of the present invention, LVAD system 10 is configured to operate in a counterpulsation mode, in which pump 24 is activated to pump blood downstream during diastole, rather than during systole in the normal operating mode described hereinabove. For example, in the configuration described hereinabove with reference to FIGS. 3A-B, control circuitry 56 is configured to activate tubular linear motor 44 to provide pulsatile flow synchronized with the cardiac cycles by, during each of the cardiac cycles: (a) activating stator 48, during at least a portion of diastole, to move magnetic piston 40 downstream during a first period of time having a first duration, and (b) activating stator 48, during at least a portion of systole, to move magnetic piston 40 upstream during a second period of time having a second duration. For some applications, the second duration is less than the first duration. The other techniques of this configuration described above may optionally be implemented, by swapping systole and diastole.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A left ventricular assist device (LVAD) system for treating a patient, the LVAD system comprising:
 (i) an implantable LVAD for implantation in the patient, the LVAD comprising:
  a stationary one-way outflow valve; and
  a pump, which (a) is shaped so as to define a pump chamber having an upstream inflow end and a downstream outflow end, and (b) comprises:
   a tubular linear motor, which comprises (1) a magnetic piston, which comprises a reciprocating one-way valve configured to allow downstream blood flow and inhibit upstream blood flow; and (2) a stator, which is configured to magnetically drive the magnetic piston with reciprocating motion, so as to pump blood downstream during downstream motion of the magnetic piston while the reciprocating one-way valve is closed;
   a spring, which is arranged to store energy during upstream motion of the magnetic piston and release the stored energy during the downstream motion of the magnetic piston;
   an outflow cannula, which is (1) couplable in fluid communication with a circulatory system of the patient at a first site, and (2) arranged in fluid communication with the downstream outflow end of the pump chamber via the stationary one-way outflow valve, wherein the stationary one-way outflow valve is configured to allow downstream blood flow from the pump chamber to the outflow cannula and to inhibit upstream blood flow from the outflow cannula to the pump chamber; and
   an inflow cannula, which is (1) couplable in fluid communication with the circulatory system at a second site upstream of the first site, and (2) arranged to allow downstream blood flow from the inflow cannula to the upstream inflow end of the pump chamber;
 (ii) a cardiac sensor, configured to sense one or more features of a plurality of cardiac cycles of a heart of the patient; and
 (iii) control circuitry, which is coupled to the cardiac sensor and configured to activate the tubular linear motor to provide pulsatile flow synchronized with the cardiac cycles by, during each of the cardiac cycles:
  activating the stator of the tubular linear motor, during a first portion of the cardiac cycle, to move the magnetic piston downstream during a first period of time, and
  activating the stator of the tubular linear motor, during a second portion of the cardiac cycle, to move the magnetic piston upstream during a second period of time,
  wherein the first portion of the cardiac cycle is at least a portion of one of systole or diastole, and the second portion of the cardiac cycle is at least a portion of the other of systole or diastole,
wherein the control circuitry and the spring are configured such that, during each of the cardiac cycles, peak power consumed by the tubular linear motor during the first portion of the cardiac cycle is no more than three times peak power consumed by the tubular linear motor during the second portion of the cardiac cycle.

2. The LVAD system according to claim 1, wherein the first period of time has a first duration, and the second period of time has a second duration greater than the first duration.

3. The LVAD system according to claim 1, wherein the spring comprises an elastic spring.

4. The LVAD system according to claim 1, wherein the spring comprises a magnetic spring.

5. The LVAD system according to claim 1,
wherein the implantable LVAD further comprises a stationary one-way inflow valve,
wherein the inflow cannula is arranged to allow the downstream blood flow from the inflow cannula to the upstream inflow end of the pump chamber via the stationary one-way inflow valve, and
wherein the stationary one-way inflow valve is configured to allow downstream blood flow from the inflow cannula to the pump chamber and to inhibit upstream blood flow from the pump chamber to the inflow cannula.

6. The LVAD system according to claim 1, further comprising a battery arranged to provide power to the tubular linear motor.

7. The LVAD system according to claim 1, wherein the control circuitry and the spring are configured such that, during each of the cardiac cycles, the peak power consumed by the tubular linear motor during the first portion of the cardiac cycle is no more than two times the peak power consumed by the tubular linear motor during the second portion of the cardiac cycle.

8. A left ventricular assist device (LVAD) system for treating a patient, the LVAD system comprising:
(i) an implantable LVAD for implantation in the patient, the LVAD comprising:
a stationary one-way outflow valve; and
a pump, which (a) is shaped so as to define a pump chamber having an upstream inflow end and a downstream outflow end, and (b) comprises:
a tubular linear motor, which comprises (1) a magnetic piston, which comprises a reciprocating one-way valve configured to allow downstream blood flow and inhibit upstream blood flow; and (2) a stator, which is configured to magnetically drive the magnetic piston with reciprocating motion, so as to pump blood downstream during downstream motion of the magnetic piston while the reciprocating one-way valve is closed;
an outflow cannula, which is (1) couplable in fluid communication with a circulatory system of the patient at a first site, and (2) arranged in fluid communication with the downstream outflow end of the pump chamber via the stationary one-way outflow valve, wherein the stationary one-way outflow valve is configured to allow downstream blood flow from the pump chamber to the outflow cannula and to inhibit upstream blood flow from the outflow cannula to the pump chamber; and
an inflow cannula, which is (1) couplable in fluid communication with the circulatory system at a second site upstream of the first site, and (2) arranged to allow downstream blood flow from the inflow cannula to the upstream inflow end of the pump chamber;
(ii) a cardiac sensor, configured to sense one or more features of a plurality of cardiac cycles of a heart of the patient;
(iii) control circuitry, which is coupled to the cardiac sensor and configured to activate the tubular linear motor to provide pulsatile flow synchronized with the cardiac cycles by:
during a first portion of each of the cardiac cycles, activating the stator of the tubular linear motor to move the magnetic piston downstream at a velocity set based on a target stroke volume and a target stroke duration, and
during a second portion of each of the cardiac cycles, activating the stator of the tubular linear motor to move the magnetic piston upstream,
wherein the first portion of each of the cardiac cycles is at least a portion of one of systole or diastole, and the second portion of each of the cardiac cycles is at least a portion of the other of systole or diastole; and
(iv) a left atrial pressure sensor, which is configured to sense left atrial pressure, wherein the control circuitry is configured to set the target stroke volume at a level that prevents the sensed left atrial pressure from exceeding a threshold pressure.

9. The LVAD system according to claim 8,
wherein the implantable LVAD further comprises a stationary one-way inflow valve,
wherein the inflow cannula is arranged to allow the downstream blood flow from the inflow cannula to the upstream inflow end of the pump chamber via the stationary one-way inflow valve, and
wherein the stationary one-way inflow valve is configured to allow downstream blood flow from the inflow cannula to the pump chamber and to inhibit upstream blood flow from the pump chamber to the inflow cannula.

10. The LVAD system according to claim 8, further comprising a battery arranged to provide power to the tubular linear motor.

11. The LVAD system according to claim 8, further comprising one or more activity sensors, which are configured to sense a level of activity of the patient, wherein the control circuitry is configured to set the target stroke volume responsively to the sensed level of activity of the patient.

12. The LVAD system according to claim 11, wherein the one or more activity sensors comprise an accelerometer, which is configured to sense the level of activity of the patient.

13. A left ventricular assist device (LVAD) system for treating a patient, the LVAD system comprising:
(i) an implantable LVAD for implantation in the patient, the LVAD comprising:
a stationary one-way outflow valve; and
a pump, which (a) is shaped so as to define a pump chamber having an upstream inflow end and a downstream outflow end, and (b) comprises:
a tubular linear motor, which comprises (1) a magnetic piston, which comprises a reciprocating one-way valve configured to allow downstream blood flow and inhibit upstream blood flow; and (2) a stator, which is configured to magnetically drive the magnetic piston with reciprocating motion, so as to pump blood downstream during downstream motion of the magnetic piston while the reciprocating one-way valve is closed;

an outflow cannula, which is (1) couplable in fluid communication with a circulatory system of the patient at a first site, and (2) arranged in fluid communication with the downstream outflow end of the pump chamber via the stationary one-way outflow valve, wherein the stationary one-way outflow valve is configured to allow downstream blood flow from the pump chamber to the outflow cannula and to inhibit upstream blood flow from the outflow cannula to the pump chamber; and an inflow cannula, which is (1) couplable in fluid communication with the circulatory system at a second site upstream of the first site, and (2) arranged to allow downstream blood flow from the inflow cannula to the upstream inflow end of the pump chamber;

(ii) a cardiac sensor, configured to sense one or more features of a plurality of cardiac cycles of a heart of the patient; and (iii) control circuitry, which is coupled to the cardiac sensor and configured to activate the tubular linear motor to provide pulsatile flow synchronized with the cardiac cycles by:

during a first portion of each of the cardiac cycles, activating the stator of the tubular linear motor to move the magnetic piston downstream at a velocity set based on a target stroke volume and a target stroke duration, and during a second portion of each of the cardiac cycles, activating the stator of the tubular linear motor to move the magnetic piston upstream, wherein the first portion of each of the cardiac cycles is at least a portion of one of systole or diastole, and the second portion of each of the cardiac cycles is at least a portion of the other of systole or diastole, wherein the LVAD system further comprises one or more activity sensors, which are configured to sense a level of activity of the patient, wherein the control circuitry is configured to set the target stroke volume responsively to the sensed level of activity of the patient, and wherein the one or more activity sensors comprise a respiration sensor, which is configured to sense the level of activity of the patient by sensing one or more parameters of respiration of the patient.

14. The LVAD system according to claim 13, wherein the respiration sensor is configured to detect transthoracic impedance.

15. A left ventricular assist device (LVAD) system for treating a patient, the LVAD system comprising:

(i) an implantable LVAD for implantation in the patient, the LVAD comprising:

a stationary one-way outflow valve; and a pump, which (a) is shaped so as to define a pump chamber having an upstream inflow end and a downstream outflow end, and (b) comprises:

a tubular linear motor, which comprises (1) a magnetic piston, which comprises a reciprocating one-way valve configured to allow downstream blood flow and inhibit upstream blood flow; and (2) a stator, which is configured to magnetically drive the magnetic piston with reciprocating motion, so as to pump blood downstream during downstream motion of the magnetic piston while the reciprocating one-way valve is closed;

an outflow cannula, which is (1) couplable in fluid communication with a circulatory system of the patient at a first site, and (2) arranged in fluid communication with the downstream outflow end of the pump chamber via the stationary one-way outflow valve, wherein the stationary one-way outflow valve is configured to allow downstream blood flow from the pump chamber to the outflow cannula and to inhibit upstream blood flow from the outflow cannula to the pump chamber; and an inflow cannula, which is (1) couplable in fluid communication with the circulatory system at a second site upstream of the first site, and (2) arranged to allow downstream blood flow from the inflow cannula to the upstream inflow end of the pump chamber;

(ii) a cardiac sensor, configured to sense one or more features of a plurality of cardiac cycles of a heart of the patient; and (iii) control circuitry, which is coupled to the cardiac sensor and configured to activate the tubular linear motor to provide pulsatile flow synchronized with the cardiac cycles by:

during a first portion of each of the cardiac cycles, activating the stator of the tubular linear motor to move the magnetic piston downstream at a velocity set based on a target stroke volume and a target stroke duration, and during a second portion of each of the cardiac cycles, activating the stator of the tubular linear motor to move the magnetic piston upstream, wherein the first portion of each of the cardiac cycles is at least a portion of one of systole or diastole, and the second portion of each of the cardiac cycles is at least a portion of the other of systole or diastole, wherein the control circuitry is configured to set the target stroke duration responsively to the sensed one or more features of the plurality of cardiac cycles.

16. The LVAD system according to claim 15, wherein the control circuitry is configured to set the target stroke duration responsively to a duration of systole of the plurality of cardiac cycles.

17. The LVAD system according to claim 16, wherein the control circuitry is configured to set the target stroke duration equal to a fraction of the duration of systole of the plurality of cardiac cycles.

18. The LVAD system according to claim 15, wherein the control circuitry is configured to set the target stroke duration responsively to a duration of diastole of the plurality of cardiac cycles.

19. The LVAD system according to claim 18, wherein the control circuitry is configured to set the target stroke duration equal to a fraction of the duration of diastole of the plurality of cardiac cycles.

* * * * *